United States Patent [19]

Berzofsky

[11] Patent Number: 5,310,657

[45] Date of Patent: May 10, 1994

[54] KINETIC ASSAY FOR ENDOTOXIN USING LIMULUS AMEBOCYTE LYSATE AND CHROMOGENIC SUBSTRATE

[75] Inventor: Ronald N. Berzofsky, Timonium, Md.

[73] Assignee: Whittaker Bioproducts, Inc., Walkersville, Md.

[21] Appl. No.: 911,375

[22] Filed: Jul. 13, 1992

Related U.S. Application Data

[62] Division of Ser. No. 428,300, Oct. 30, 1989, abandoned.

[51] Int. Cl.$^5$ .............. F27B 9/40; F27B 14/00; F27B 9/12; F27D 7/00
[52] U.S. Cl. ............................... 435/34; 435/4; 435/13; 435/18; 435/23; 435/38; 930/DIG. 785
[58] Field of Search .............. 435/4, 13, 18, 23, 34, 435/38; 930/DIG. 785

[56] References Cited

U.S. PATENT DOCUMENTS

| | | | |
|---|---|---|---|
| 4,188,264 | 2/1980 | Iwanaga et al. | 435/23 |
| 4,322,217 | 3/1982 | Dikeman | 435/29 |
| 4,406,832 | 9/1983 | Mills | 435/23 |
| 4,510,241 | 4/1985 | Mills | 435/23 |
| 4,663,298 | 5/1987 | Urbascheck et al. | 435/4 |

FOREIGN PATENT DOCUMENTS

| | | |
|---|---|---|
| 0074761 | 9/1982 | European Pat. Off. |
| 0180905 | 10/1985 | European Pat. Off. |
| 2740323 | 12/1978 | Fed. Rep. of Germany |
| 2080524 | 2/1982 | United Kingdom |

OTHER PUBLICATIONS

Numazawa, R. et al., "Endotoxin-Detecting Device", Chemical Abstracts, CA 102(3):19426q, 1984.
Seihagaken Kogyo Co., "Reagents for Detection of Bacterial Endotoxins", Chemical Abstracts, CA 95(9):75210p, 1981.
Dolan et al., "Clinical Evaluation of the Plasma Chronozenic Limulus Assay", from *Detection of Bacterial Endotoxins with the Limulus*, 1987, pp. 405–416.
Levin et al., "Clottable Protein in Limulus: Its Localization and Kinetics of Its Coagulation by Endotoxin", Thromb. Diath. Haemorrh., (1968), 19:186–197.
Ditter et al., "Detection of Endotoxin in Blood and Other Specimens by Evaluation of Photometrically Registered LaL-Reaction-Kinetics in Microtiter Plates", Endotoxins and Their Detection with the Limulus Amebocyte Lysate Test, in Alan R. Lisk, Inc., New York, pp. 385–392 (1982).
Urbaschek et al., "Protective Effects and Role of Endotoxin in Experimental Septicemia", Circul. Shock, (1984), 14:209–222.
Lindsay et al., "Single-Step, Chromogenic Limulus Amebocyte Lysate Assay for Endotoxin", J. Clin. Microbiol., (1989), 27:947–951.
Young et al., "An Invertebrate Coagulation System Activated by Endotoxin: Evidence for Enzymatic Mediation", J. Clin. Invest., (1972), 51:1790–1797.
Nakamura et al., "Amino Acid Sequence on the Fragments Produced from Horseshoe Crab Coagulogen During Gel Formation: Homologies with Primate Fibrinopeptide B", Biochem. Biophys. Res. Comm., (1976), 72:902–908.
Iwanaga et al., "Chromogenic Substrate for Horseshoe Crab Clotting Enzyme, Its Application for the Assay of Bacterial Endotoxin", Haemostasis, (1978), 7:183–188.

(List continued on next page.)

*Primary Examiner*—Michael G. Wityshyn
*Assistant Examiner*—T. J. Reardon
*Attorney, Agent, or Firm*—Banner, Birch, McKie & Beckett

[57] ABSTRACT

A kinetic assay procedure is provided which permits measurement of endotoxin concentration in the range from 0.005 EU/ml to 50 EU/ml. The assay procedure relies on a single reagent substrate composition comprising *Limulus amebocyte* lysate and a chromogenic substrate. This assay procedure is easily automated and it provides substantial improvement in both range and sensitivity over previously available endotoxin assays.

5 Claims, No Drawings

OTHER PUBLICATIONS

Novitsky et al., "Design Criteria and Evaluation of the LaL-4000 for Kinetic Turbidimetric LAL Assay", in Detection of Bacterial Endotoxins with the Limulus Amebocyte Lysate Test, pp. 189–196, Prog. Clin. Biol. Res., vol. 231 (1987).

Remillard et al., "Quantitation of Endotoxin in Products Using the LAL Kinetic Turbidimetric Assay", in Detection of Bacterial Endotoxins with the Limulus Amebocyte Lysate Test, pp. 197–210, Prog. Clin. Biol. Res., vol. 231 (1987).

Friberger et al., "Colorimetric Method", Methods of Enzymatic Analysis, vol. XI, pp. 107–117 (1986).
CALBIOCHEM Corporation Catalog, p. 341.

KINETIC ASSAY FOR ENDOTOXIN USING LIMULUS AMEBOCYTE LYSATE AND CHROMOGENIC SUBSTRATE

This application is a continuation of application Ser. No. 07/428,300, filed Oct. 30, 1989, now abandoned.

BACKGROUND OF THE INVENTION

1. Field of the Invention

This invention concerns the determination of endotoxin in fluids using a *Limulus amebocyte* lysate based assay.

2. Description of Related Art

The coagulation phenomena of the pro-clotting enzyme of the amebocyte lysate from the blood of the horseshoe crab by bacterial endotoxin has been known and reported for many years, see, for example Levin, J. and Bangs, F. B., "Clottable Protein in Limulus: Its Localization and Kinetics of its Coagulation by Endotoxin," Thomb. Diath. Heamortz. 19, pg. 186 (1968). The clotting mechanism has been subject to in-depth studies such as the study by Nakamura, S. et al., "Amino Acid Sequence Studies on the Fragments Produced from Horseshoe Crab Coagulogen during Gel Formation: Homologies with Primate Fibrinopeptide B", Biochemical and Biophysical Research Communication, 72(3), p. 902 (1976).

The coagulation of *Limulus amebocyte* lysate, hereinafter LAL, involves the endotoxin activation of a pro-clotting enzyme in the presence of divalent cations, e.g. $Ca^{++}$, $Mg^{++}$, $Sr^{++}$ or $Mn^{++}$, with the resulting activated enzyme cleaving a clotting protein (coagulogen) at the C-carboxyls of contained glycine and arginine units. The cleaved units of the coagulogen remain attached by disulfide bridges and undergo polymerization to effect a clot. In addition to these known components of the amebocyte lysate, there are many other proteins and a known inhibitor of a lipoprotein nature. The mechanism of modulation of the coagulation reaction by the inhibitor and other proteins has not yet been determined.

Because of the coagulation characteristic of LAL in the presence of bacterial endotoxin (pyrogen), LAL formulations have become commercially important reagents for use in endotoxin assays for quality control in the manufacture of various fluids of pharmaceutical or medical interest which are normally administered parenterally. Such fluids include water for injection; water for irrigation; lipid emulsions for intravenous feeding; aqueous emulsions of vegetable oil; salt solutions, e.g. parenterally administered sodium chloride solutions including sodium chloride for injection USP, sodium chloride for irrigation USP, sodium chloride for inhalation, and lactated Ringer's solution; and blood derivatives, e.g., normal serum albumin, plasma protein fraction and anti-hemophilic factor USP, immune globulin, Rho(D) immune globulin and antihuman globulin serum.

The formulation of LAL reagents and the improvement in LAL procedures has progressed to the point that an LAL assay is the most sensitive and practical endotoxin test that is known. The LAL assay can detect, with the formation of a clot, as little as $10^{-12}$ grams/ml of endotoxin. A Health Industries Association Study [Dabah, et al., "HIMA Collaborative Study for the Pyrogenicity Evaluation of a Reference Endotoxin by the USP Rabbit Test", HIMA Document No. 7, vol. 1 (May, 1979)] showed that the United States Pharmacopeia (USP) rabbit pyrogen assay can detect approximately $10^{-9}$ grams/ml of endotoxin. Therefore, the LAL assay is approximately 100 times as sensitive as the USP rabbit pyrogen assay. In addition to its advantage of sensitivity, the LAL assay is simpler to perform and can be completed in approximately one hour as opposed to three hours for the rabbit assay.

The assay of endotoxin detected by clotting of LAL is essentially a kinetic assay. Endotoxin activates the clotting enzyme, the clotting enzyme cleaves the coagulogen, and the cleaved coagulation aggregates to form a gel. More endotoxin results in more rapid accumulation of cleaved coagulogen and in faster gel formation, and so the time required to form the gel is less when more endotoxin is present. In other words, the endotoxin concentration is inversely related to the gelling time in the assay.

There are difficulties associated with precise determination of clotting time, as required by this assay methodology. Aggregation, flocculation and clotting are successive stages in a complex physical phenomenon involving a multiplicity of physical forces and probably multiple components. The boundaries between the stages are not clearly marked, but rather they are subjectively established and can differ when established by different observers. LAL is a chemically complex mixture, and apparently small changes in composition can have profound effects on the course of the complex coagulation phenomenon. Finally, an assay based on the subjective determination of gel formation is inherently difficult to automate. An alternative assay methodology was developed to overcome some of the difficulties associated with accurately determining gel formation and the associated endotoxin concentration.

The use of chromogenic substrates has become a means to both study and clinically monitor various enzymes and inhibitors in the complex coagulation processes of man. An extensive list of enzyme specific substrates are commercially available for measuring enzymes such as trypsin, thrombin, thromboplastin, plasmin, Kalikrein, Urokinase, and plasminogen. These synthetic substrates provide the investigator with an important tool to monitor the hemostatic state of certain aspects of the coagulation process in vitro.

Iwanaga, et al., "Chromogenic Substrates for Horseshoe Crab Clotting Enzyme: Its application for the Assay of Bacterial Endotoxin", Hemostasis 7:183-188 (1978), report that synthetic substrates can be used to measure the level of endotoxin activated pro-clotting enzyme in LAL prepared from the blood of both the Japanese (*Tachypleus tridentatus*) and the American (*Limulus polyphemus*) horseshoe crabs. One advantage of chromogenic substrates in an LAL assay relative to a conventional LAL gelation test is that the amount of activated clotting enzyme can be quantified. The use of certain synthetic peptide-type substrates in LAL assay to measure bacterial endotoxins quantitatively has been described in U.S. Pat. No. 4,188,264. The disclosure of the patent teaches a peptide substrate with a structure consisting of L-amino acids in the sequence $R_1$-gly-arg-$R_2$ where $R_1$ represents an N-blocked amino acid and $R_2$ is a group which can be released by enzymatic hydrolysis to yield a colored compound, $HR_2$.

Another patent, U.S. Pat. No. 4,510,241, discloses an improved chromogenic peptide substrate for use in LAL-type assays. This improved substrate differs most significantly from the previous substrate in that the gly moiety is replaced in the sequence by ala or cys.

During an LAL-type assay using one of these substrates, the pro-clotting enzyme (a serine protease) in the LAL is activated by endotoxin and cleaves the peptide chain on the carboxyl side of arginine so as to release the chromogenic group and form a marker compound which can be easily read by means such as spectrophotometry.

A number of drawbacks to the LAL assay remain, despite numerous modifications designed to improve quantitation, sensitivity, speed, and precision. Foremost among these is the limited range of sensitivity (about 1 order of magnitude) with either the turbidimetric or the chromogenic fixed incubation time (endpoint method). A second drawback to endpoint methods is the requirement that an operator must end or read the reaction at a precise time. In the chromogenic test, acid must be added to stop the test. The optical density can be read in a spectrophotometer at any time thereafter. In the endpoint turbidimetric method, the reaction cannot be stopped without destroying the turbidity but must be read immediately after a specific incubation period.

An alternative approach to improving the LAL-type assay was to improve the precision of measuring the coagulation phenomenon. This was done by focusing on the increase in turbidity of the assay solution as aggregation proceeded, rather than waiting for gelation (Young, et al., (1972) *J. Clin. Invest.*, 51:1790–1797). The kinetic turbidimetric LAL assay provides several potential improvements over endpoint methodology. The kinetic turbidimetric method uses a single reagent and does not require operator attention after initiation of the test, thus precision, speed, and accuracy are all improved. Most importantly, the range of the test could be increased from 1 to greater than 5 orders of magnitude. Unfortunately, turbidity determinations made with a spectrophotometer use the decrease in transmitted light caused by physical blocking, and thus Beer's law does not apply. Particle size and number, and reflected and refracted light all affect measurement to various degrees. Though elegant electronic filtering coupled with computer smoothing of data have been successfully developed and used for interpreting kinetic turbidity results (Novitsky, et al., p. 189–196, and Remillard, et al., pp. 197–210, both in Watson, et al., "Detection of Bacterial Endotoxins with the Limulus Amebocyte Lysate Test," Alan R. Liss, Inc., New York, 1987), these methods are available only on specialized optical readers. In addition, some products must be diluted extensively to be assayed at all with the kinetic turbidimetric method.

SUMMARY OF THE INVENTION

It is an object of this invention to provide a method of assaying endotoxin having enhanced sensitivity.

It is a further object of this invention to provide a method of assaying endotoxin which is applicable over an increased range of endotoxin concentrations in the fluid of interest.

It is yet another object of this invention to provide a method of assaying endotoxin which reduces assay errors.

It is still another object of this invention to provide a kinetic assay substrate composition.

These and other objects are provided by the following embodiments of this invention.

This invention contemplates an assay method for endotoxin based on activation of the pro-clotting enzyme in LAL by endotoxin and detection of the activated clotting enzyme by cleavage of chromogenic substrates, using a kinetic procedure. To facilitate the kinetic procedure, this invention provides a kinetic assay substrate composition comprising a mixture of a *Limulus amebocyte* lysate reagent and a chromogenic substrate. By use of this substrate composition and a kinetic procedure for the determination, the detection limit for endotoxin is lowered from one-to-three orders of magnitude, and the range of detectable endotoxin concentrations is increased by at least two orders of magnitude, compared with prior endotoxin assays based on LAL and chromogenic substrates. Also, the assay method of this invention does not require further manipulation once the endotoxin-containing sample has been mixed with the kinetic substrate composition, so error introduced by manipulation is substantially reduced.

DETAILED DESCRIPTION

The Substrate Composition for the Kinetic Assay

The improved endotoxin assay method of this invention is based on the use of a novel substrate composition that provides enhanced sensitivity and a broader assay range as well as decreased potential for operator-induced error during the procedure. The novel substrate composition for the kinetic assay procedure of the present invention comprises, as a single reagent, a mixture of: (1) a *Limulus amebocyte* lysate reagent containing both the lysate extracted from horseshoe crab amebocytes and a surfactant which enhances sensitivity, (2) a chromogenic substrate and (3) optionally other salts and buffers.

While any *Limulus amebocyte* lysate (LAL) reagent can be used in the practice of this invention, LAL reagent prepared according to U.S. Pat. No. 4,322,217, which is hereby incorporated by reference, provides exceptional results. The preferred LAL reagent contains between 1 and 4 mg *Limulus amebocyte* lysate protein/ml and between 0.01 and 0.05% (w/v) of surfactant capable of inactivating the inhibitor present in Limulus blood, preferably diluted in Tris/MgCl$_2$/NaCl buffer, pH 7.0–7.5. A particularly preferred surfactant is Zwittergent® 3-14, N-tetradecyl-N,N-dimethyl-3-ammonio-1-propanesulfonate (Calbiochem, Inc.).

Once again, any chromogenic substrate which is cleaved by the clotting enzyme may be used in this invention. However, the chromogenic substrate prepared according to U.S. Pat. No. 4,510,241, which is hereby incorporated by reference, provides exceptional results. The most preferred substrate comprises the sequence: acetate-Ile-Glu-Ala-Arg-pNA where pNA represents a para-nitroaniline group. The concentration and composition of chromogenic substrate solution is within the skill of the art. A typical chromogenic substrate solution comprises between 0.5 and 4 mg/ml of chromogenic substrate (equivalent to 1.4 to 11 micromoles/ml) prepared in Tris/MgCl$_2$/NaCl buffer, pH 7.0–7.5.

Chromogenic substrates with the formula $R_1$-gly-arg-$R_2$ provide adequate changes in absorbance for use in the kinetic assay described below, but they have been observed by the inventor to result in rapidly changing baselines. (This may be the result of autohydrolysis of the substrate at the neutral pH conditions optimum for the kinetic assay, so that clotting enzyme activation and hydrolysis of the chromogenic substrate can occur simultaneously.) Although kinetic assays performed using this chromogenic substrate cover a wider range than the endpoint assays of the prior art, this elevated baseline limits their ability to measure low concentrations of endotoxin. In contrast, kinetic assays run with the preferred substrates (taught in U.S. Pat. No. 4,510,241) show much more stable baselines and consequently higher sensitivity, resulting in improved assay performance with samples or dilutions containing very low endotoxin concentrations. Similarly, LAL prepared by the preferred method, taught in U.S. Pat. No. 4,322,217, provides additional enhancement in sensitivity of the kinetic assay over other LAL preparations, but kinetic assays run with any of the commercially available LAL preparations show improved range and sensitivity relative to the chromogenic endpoint assays available in the prior art.

As will be apparent to one of ordinary skill, divalent metal salts, which are known to promote activation of the pro-clotting enzyme will preferably be present, as well as buffers to avoid extremes of pH that could inactivate the clotting enzyme. Any of the buffers and salts, which are taught in the art to be compatible with the LAL system, may be used. A preferred buffer system comprises the buffer Tris (tris(hydroxy)aminomethane) with the salts $MgCl_2$ and NaCl, and as indicated above, this buffer system may be used to prepare the LAL reagent and to dissolve the chromogenic substrate.

The LAL reagent and the chromogenic substrate solution may be prepared independently. They may be stored at 2°-8° C. until finally formulated for use. The kinetic assay substrate composition used in the assay is a mixture of the two above solutions. The preferred ratio is 30 parts LAL solution to 70 parts chromogenic substrate solution.

As will be apparent to one skilled in the art, the amounts of LAL protein and of chromogenic substrate present in the kinetic assay substrate composition will be adjusted to ensure that effective amounts of these two components are present in the reaction or assay mixture after addition of sample. In this final mixture during the endotoxin assay, the concentration of LAL protein is from about 0.15 to about 0.6 mg/ml, preferably from about 0.3 to about 0.5 mg/ml. The concentration of the chromogenic substrate in the assay is from about 0.5 mM to about 3.9 mM, preferably about 1.0 mM.

In a preferred mode the substrate composition containing the LAL reagent and the chromogenic substrate is filled into vials and lyophilized using standard lyophilization procedures well known to those of ordinary skill in the art. This lyophilized material is substantially free of water (less than 5%) and may be stored at room temperature but preferably is stored refrigerated (0°-4° C.). The substrate composition is reconstituted immediately prior to use for the assay by adding a volume of sterile, pyrogen-free water into the vial to dissolve the lyophilized material. The volume of water added is such that the concentration of solids which was present prior to lyophilization will be attained in the reconstituted composition.

A reagent kit for use in performing kinetic assays for determination of endotoxin should comprise one or more vials in which the kinetic assay substrate composition comprising the chromogenic substrate and the LAL has been lyophylized. In addition, the reagent kit could contain vials of other reagents which are useful in the kinetic assay of endotoxin, such as pyrogen-free water for diluting samples and standardized endotoxin solution for the preparation of standard curves.

Kinetic Assay Method

The present method utilizes the initial part of the LAL endotoxin reaction to activate an enzyme present in the LAL which in turn releases a colored moiety from a synthetic substrate, producing a detectable color change in the reaction mixture. To determine the amount of Gram negative bacterial endotoxin in a material, a sample of the material is mixed with the above described chromogen-LAL substrate composition in a cuvette, microplate or similar vessel for spectrophotometric determination. Gram negative bacterial endotoxin catalyzes the activation of a proenzyme in the Limulus Amebocyte Lysate (LAL). The initial rate of activation is determined by the concentration of endotoxin present. The activated enzyme catalyzes the splitting of a colored moiety from the colorless substrate, and the reaction is monitored spectrophotometrically over time to record the time-variable appearance of a detectable color change. The time required for a color change of any particular magnitude (Reaction Time) is inversely related to the amount of endotoxin present. That is, in the presence of a large amount of endotoxin the reaction occurs rapidly and thus a given change in color occurs in a shorter time period. In the presence of a smaller amount of endotoxin the reaction time is increased and the color changes more slowly.

The concentration of endotoxin in unknown samples can be calculated from a standard curve prepared using a series of samples of known endotoxin concentration. A log/log correlation between the time required for a certain degree of color to appear (Reaction Time) and the endotoxin concentration is linear from 0.005 to 50 EU/ml. The concentration of endotoxin in a sample is calculated from its Reaction Time by comparison to the Reaction Time of solutions containing known amounts of endotoxin standard.

Specimen Collection and Preparation

The endotoxin assay method based on kinetic procedures may be used to determine endotoxin in any fluids of pharmaceutical or medical interest where endotoxin determination is currently performed by any other method. This includes, but is not limited to water for injection; water for irrigation; lipid emulsions for intravenous feeding; aqueous emulsions of vegetable oil; salt solutions, e.g. parenterally administered sodium chloride solutions including sodium chloride for injection USP, sodium chloride for irrigation USP, sodium chloride for inhalation, and lactated Ringer's solution; and blood derivatives, e.g., normal serum albumin, plasma protein fraction and anti-hemophilic factor USP, immune globulin, Rho(D) immune globulin and antihuman globulin serum. This method may also be used to detect endotoxin in biological fluids where the presence of endotoxin may be of diagnostic significance including, but not limited to blood, lymph, urine, serum, acites fluid, lung aspirants and the like.

All materials coming in contact with the specimen or test reagents must be pyrogen-free. Materials may be rendered pyrogen-free by heating at 250° C. for 30 minutes. Appropriate precautions should be taken to protect depyrogenated materials from subsequent environmental contamination. It may be necessary to adjust the pH of the sample to within the range 7.0-8.0 using pyrogen-free sodium hydroxide or hydrochloric acid.

Samples to be tested should be stored in such a way that all bacteriological activity is stopped or the endotoxin level may increase with time. For example, store samples at 2°-8° C. for less than 24 hours; samples stored longer than 24 hours should be frozen.

Assay Procedure

The assay is initiated by mixing an aliquot (sample) of the test fluid with a present volume of the kinetic assay substrate composition. The final volume of the resultant assay mixture will be determined based on the requirements of the specific spectrophotometer used to monitor changes in absorbance over the course of the reaction. The ratio of volumes between the sample and the substrate composition can be easily established by those of ordinary skill in the art to provide for convenient pipetting. Depending on the relative volumes added to the assay mixture, the concentration of the components in the kinetic assay substrate composition will be adjusted to maintain the final concentrations in assay mixture in the operable range as defined above.

After mixing the sample and the substrate composition, the assay mixture is placed in a spectrophotometer, and the optical density at the wave length characteristic of the chromogenic substrate used is recorded at discrete time points at least until the absorbance change relative to the initial absorbance reading exceeds a predetermined value, where said value is selected to balance the need for sensitivity (large absorbance changes) against the need to complete the assay in order to free the spectrophotometer for subsequent use (small absorbance changes). The balance between these factors will vary depending on the test fluid used, as will be apparent to those of ordinary skill in the art.

In a preferred mode, the spectrophotometer is a programmable microplate reader available in the art, and the volume of the mixture will be determined by the size of the wells in the microplate. Multiple samples of various test fluids, as well as the series of endotoxin dilutions making up a standard curve, may be placed in the wells of a microplate. Then a fixed amount of the substrate composition is added to each of the wells, preferably with a multipipetor, and the plate processed by the microplate reader which is programmed to sequentially read the absorbance of each well in repetitive fashion.

Calculation of Endotoxin Concentration

Continuously throughout the assay, the absorbance is monitored by spectrophotometry. Using the initial absorbance reading of the mixture as its own blank, for example, the time required for the absorbance to increase by a specific amount, preferably equal to or greater than 0.200 absorbance units, is determined. This time is termed Reaction Time.

The Reaction Time for each sample of each product corresponds to the endotoxin concentration for that sample. The absolute value of endotoxin concentration for the sample is determined by comparison of the Reaction Time for the sample with the Reaction Time for at least one control solution whose endotoxin concentration is known. The ratio of Reaction Times (time for absorbance to change by a preset amount) for the unknown relative to the known sample is inversely proportional to the ratio of their concentrations.

A preferred method of determining endotoxin concentration for an unknown sample is to compare the log of the Reaction Time of the unknown to a standard curve consisting of a plot of the log (Reaction Time) of a series of samples with known endotoxin concentration against the log (endotoxin concentration) for the same samples.

Because of the large concentration range over which endotoxin values can be determine, it is possible to adjust the quantitative range of any given assay by adjusting the concentration of endotoxin standards used to generate curve. The table below suggests a dilution scheme for constructing a series of endotoxin dilutions from an endotoxin standard of known endotoxin activity. Not all dilutions must be used to generate a standard curve. Alternative dilution schemes can be used as well.

TABLE I

| Endotoxin Concentration (EU/ml) | Volume of Pyrogen-Free Water | Volume of Endotoxin Solution added to Pyrogen-Free Water |
|---|---|---|
| 5 | 0.1 ml | 0.9 ml of 50 EU/ml solution |
| 0.5 | 0.1 ml | 0.9 ml of 5 EU/ml solution |
| 0.05 | 0.1 ml | 0.9 ml of 0.5 EU/ml solution |
| 0.005 | 0.1 ml | 0.9 ml of 0.05 EU/ml solution |

A preferred procedure for preparation of control samples comprises:

1. Prepare a solution containing 5 EU/ml endotoxin by addition 0.1 ml of a 50 EU/ml endotoxin stock into 0.9 ml of pyrogen-free water. This solution should be vigorously vortexed for at least 1 minute before proceeding.

2. Transfer 0.1 ml of the 1 EU/ml endotoxin solution into 0.9 ml of pyrogen-free water in a suitable container and label 0.5 EU/ml. The solution should be vigorously vortexed for at least 1 minute before proceeding.

3. Transfer 0.1 ml of the 0.5 EU/ml endotoxin solution into 0.9 ml of pyrogen-free water in a suitable container and label 0.05 EU/ml. This solution should be vigorously vortexed for at least 1 minute before proceeding.

4. Transfer 0.1 ml of the 0.05 EU/ml endotoxin solution into 0.9 ml of pyrogen-free water in a suitable container and label 0.005 EU/ml. This solution should be vigorously vortexed for at least 1 minute before proceeding.

Product Inhibition by Other Components in the Test Solution

Inhibition occurs when substances in the test sample interfere with the LAL reaction. In the method of this invention, such inhibition results in a longer Reaction Time, indicating lower levels of endotoxin than may actually be present in the test sample, either undiluted or at an appropriate dilution.

To verify the lack of inhibition, an aliquot of test sample (or a dilution of test sample) is spiked with a known amount of endotoxin.

It is recommended that the endotoxin spike result in a final endotoxin concentration in the sample equal to the mid-point, on a log basis, between the endotoxin concentration of the highest and lowest standards in the standard curve.

For example, in an assay with a standard curve spanning from 50 to 0.005 EU/ml, samples should be spiked to contain a final endotoxin concentration of 0.5 EU/ml.

| | | |
|---|---|---|
| log 50 | = | 1.6990 |
| log 0.005 | = | −2.3010 |
| log average | = | −0.3010 |
| antilog | = | 0.5 |

In an assay with a standard curve spanning from 1 to 0.01 EU/ml, the endotoxin spike should result is a final endotoxin concentration of 0.1 EU/ml.

| | | |
|---|---|---|
| log 1.0 | = | 0.0000 |
| log 0.01 | = | −2.0000 |
| log average | = | −1.0000 |
| antilog | = | 0.1 |

The spiked solution is assayed in parallel with the unspiked sample and their respective endotoxin concentrations, as well as the endotoxin recovered in the spiked sample are calculated. The endotoxin recovered should equal the known concentration of the spike ±25%.

If the test sample (or dilution) is found to be inhibitory to the reaction, the sample may require further dilution until the inhibition is overcome.

Initially, one may want to screen for inhibition by testing 10-fold dilutions of test sample. Once the approximate non-inhibitory dilution is determined, the exact dilution can be found by testing two-fold dilutions around this dilution.

The degree of inhibition or enhancement will be dependent upon the concentration of the test solution. If several concentrations of the same solution are to be assayed, it is necessary to establish performance characteristics for each independently.

Patterns of inhibition or enhancement different from those seem with the traditional LAL gelation test may be found.

It may be necessary to adjust the pH of the sample to within the range 7.0 to 8.0 using pyrogen-free sodium hydroxide or hydrochloric acid to overcome inhibition.

Colored Samples

Since the initial absorbance reading of each sample is used as its own blank, samples which possess significant color on their own do not present a special problem. However, if the background color is 1.5 absorbance units, the sample should be diluted and reassayed.

EXAMPLE 1

Preparation of kinetic assay substrate composition, lyophilized in vials. Bulk chromogenic substrate is dissolved in chilled (0°–4° C.), autoclaved, endotoxin-free Tris-MgCl$_2$-NaCl buffer and Sterile Water for Injection, USP. The resultant solution is depyrogenated by ultrafiltration and sterilized by aseptic filtration. The chromogenic substrate solution is stored refrigerated (0°–4° C.) until needed.

Undiluted lysate is removed from refrigeration and formulated to the desired level of activity by adding a chilled (0°–4 C.) solution of autoclaved endotoxin-free Tris-MgCl$_2$-NaCl buffer, Zwittergent TM 3-14 solution and Sterile Water for Injection USP. The resultant diluted bulk lysate is mixed well and refrigerated (0°–4° C.).

Bulk diluted lysate is aseptically combined with chromogenic substrate solution by mixing 30 parts bulk diluted lysate with 70 parts chromogenic substrate solution.

The combined LAL/Substrate reagent is aseptically dispensed (2.6±0.2 ml) in a separate area equipped with laminar flow HEPA filtration. Following dispensing, the final containers are partially stoppered with the appropriate lyophilization stopper, placed in the lyophilizer and lyophilized as described below.

The product is placed on the shelf, allowed to freeze and the condenser is cooled to −40° C. or below. The chamber is placed under vacuum and the product is sublimated with a final drying cycle set to ensure a product residual moisture of 5.0% or less.

TABLE II

THE COMPOSITION OF THE REAGENT
Co-lyophilized Lystate/Substrate
The Name and Amount of Each Ingredient in Co-lyophilized
Limulus Amebocyte Lysate/Chromogenic Substrate Reagent.

| | per ml | per 2.6 ml vial |
|---|---|---|
| Limulus Amebocyte Lysate | 0.6 mg | 1.56 mg |
| Chromogenic Substrate, N—Ac—Ile—Glu—Ala—Arg—pNA (acetate salt) | 0.7 mg | 1.82 mg |
| Zwittergent TM 3-14* | 0.06 mg | 0.16 mg |
| Magnesium Chloride 6H$^2$O | 2.0 mg | 5.2 mg |
| Sodium Chloride | 4.5 mg | 11.7 mg |
| Tris (hydroxyethyl) Aminomethane | 6.06 mg | 15.76 mg |
| Sterile Water for Injection, USP | qs 1.00 mg | qs 2.60 ml |

*A surfactant - trademark of Calbiochem, Inc., quantity is adjusted for each lot to obtain optimum chromogenic activity.

EXAMPLE 2

A standard curve using the kinetically-based endotoxin assay with chromogenic substrate. 100 ul of co-lyophilized LAL:substrate reagent prepared in Example 1 was mixed with 100 ul of various dilutions of the U.S. reference endotoxin preparation, EC-5, in individual wells of a 96-well microplate. The microplate was incubated at 37 C. in the Kinetic-QCL TM reader, absorbance values at 405 nm were recorded at 120 second intervals.

The absorbance of each sample (dilution) was plotted against time. From these curves, the Reaction Time (time required to reach 0.2 absorbance units) was determined for each sample and is shown in Table III. The standard curve in the plot of log (Reaction Time) vs. log (endotoxin concentration) for these samples.

EXAMPLE 3

Three pilot lots of the co-lyophilized LAL/substrate reagent were produced according to Example 1. Standard curves were generated for each lot according to the procedure described in Example 2, and the data for Reaction Time at each endotoxin concentration is listed in Table III for one of the lots.

Table III summarizes the variation seen within replicates (N=3) of the endotoxin standards used to generate the standard curves. In all cases the coefficient of variation is less than 5.0%.

TABLE III

Variability Within Replicates of Endotoxin Standards

| Standard | Substrate Composition of Example 2 | | | Substrate Composition of Example 3 | | |
|---|---|---|---|---|---|---|
| (EU/ML) | Mean | S. Dev. | CV | Mean | S. Dev. | CV |
| 0.005 | 2839 | 58.5 | 2.1% | 4014 | 37.7 | 0.9% |
| 0.01 | 2668 | 70.6 | 2.6% | 3515 | 18.1 | 0.5% |
| 0.05 | 1758 | 18.8 | 1.1% | 2277 | 8.5 | 0.4% |
| 0.1 | 1456 | 8.7 | 0.6% | 1997 | 14.4 | 0.7% |
| 0.5 | 924 | 5.1 | 0.6% | 1334 | 11.9 | 0.9% |
| 1.0 | 758 | 3.0 | 0.4% | 1175 | 13.5 | 1.1% |
| 10.0 | 441 | 4 | 0.9% | 726 | 12.4 | 1.7% |
| 20.0 | N.D. | N.D. | N.D. | 624 | 4.9 | 0.8% |

EXAMPLE 4

The log/log correlation and computation of endotoxin concentration in unknowns. The indicated samples and standards were assayed for endotoxin according to the procedure described in Example 2.

TABLE IV

EXAMPLE CALCULATIONS

| Standards | Concentration | Mean Reaction Time (sec) | Log Concentration | Log Mean Reaction Time |
|---|---|---|---|---|
| Blank | — | Unreactive | — | — |
| 1 | 0.005 EU/ml | 2675 | −2.301 | 3.427 |
| 2 | 0.050 EU/ml | 1780 | −1.301 | 3.250 |
| 3 | 0.100 EU/ml | 1529 | −1.000 | 3.184 |
| 4 | 0.500 EU/ml | 1090 | −0.301 | 3.021 |
| 5 | 1.000 EU/ml | 922 | 0.000 | 2.985 |
| 6 | 10.000 EU/ml | 526 | 1.000 | 2.721 |
| 7 | 50.000 EU/ml | 398 | 1.699 | 2.600 |
| Samples | | | | |
| 1 | — | 1576 | — | 3.198 |
| 2 | — | 943 | — | 2.975 |

Standard Curve by least-squares regression: log (Mean Reaction Time) = −0.213 × (log (concentration)) +2.957
Sample 1: log (mean time) of 3.198 corresponds to log (concentration) of −1.131 or 0.074 EU/ml.
Sample 2: log (mean time) of 2.975 corresponds to log (concentration) of 0.085 or 0.823 EU/ml.

EXAMPLE 5

A kit for kinetic assay of endotoxin can be assembled containing the following:
8 vials prepared as described in Example 2
2 vials containing *E. coli* endotoxin standardized against Reference Standard Endotoxin *E. coli* lot EC-5 (Center for Biological Evaluation and Research, U.S. Food and Drug Administration)
3 vials containing Pyrogen Free Water
1 set instructions describing the kinetic assay procedure and standard curve preparation.

I claim:

1. A kinetic method for determination of endotoxin in a test fluid using a kinetic assay substrate composition comprising the steps of:
   (a) mixing a sample of the test fluid with a kinetic assay substrate composition containing a chromogenic substrate of the clotting enzyme of *Limulus amebocyte* lysate and a *Limulus amebocyte* lysate comprising a pro-clotting enzyme and having sensitivity to endotoxin in a vessel containing a spectrophotometric path under conditions suitable for endotoxin assay to form a sample-kinetic assay substrate composition mixture, wherein both said chromogenic substrate and said lysate are present in an endotoxin determining amount;
   (b) placing said vessel in a spectrophotometer so that the spectrophotometer beam passes through the vessel and the sample-kinetic assay substrate composition mixture;
   (c) monitoring the change in optical absorbance of this sample-kinetic assay substrate composition mixture over time;
   (d) determining the time required for a predetermined absorbance change to occur, wherein said predetermined absorbance change optimizes assay sensitivity and assay duration;
   (e) calculating endotoxin concentration in the sample by comparison of said time to a standard curve obtained by correlating the concentration of endotoxin in standard endotoxin solutions with the time required to reach said predetermined absorbance change for each standard endotoxin solution, wherein said standard endotoxin solutions are mixed with said kinetic assay substrate composition under conditions suitable for endotoxin assay before determining the time required for the predetermined absorbance change to occur.

2. The method of claim 1 wherein said chromogenic substrate has the formula:

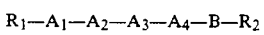

wherein $R_1$ represents hydrogen, a blocking aromatic hydrocarbon or acyl; $A_1$ represents an L or D-amino acid selected from Ileu, Val or Leu; $A_2$ represents Glu or Asp; $A_3$ represents Ala or Cyst; $A_4$ represents Arg; B represents a linkage selected from ester and amide; and $R_2$ represents a chromogenic or fluorogenic group which is covalently attached to the C-carboxyl terminal of arginine through the B linkage, the fluorogenic or chromogenic moiety being capable of being enzymatically cleaved from the remainder of the chromogenic substrate in the presence of endotoxin and pro-clotting enzyme to form a chromogen or a fluorogen.

3. The method of claim 1 wherein the *Limulus amebocyte* lysate has decreased sensitivity due to the presence of an endogenous inhibitor and said kinetic assay substrate composition contains a sensitivity enhancing amount of an inactivating surfactant for the inhibitor.

4. The method of claim 2 wherein the *Limulus amebocyte* lysate has decreased sensitivity due to the presence of an endogenous inhibitor and said kinetic assay substrate composition contains a sensitivity enhancing amount of an inactivating surfactant for the inhibitor.

5. The method of claim 3 where the vessel is a microtiter plate wherein multiple sample-kinetic assay substrate composition mixtures are present in multiple wells and the spectrophotometer is a microtiter plate reader which monitors each well sequentially in a repeating pattern.

* * * * *